(12) United States Patent
Maudsley

(10) Patent No.: US 6,228,357 B1
(45) Date of Patent: May 8, 2001

(54) CANCER THERAPY USING AN ONCOGENE PRODUCT AND A FOREIGN MHC MOLECULE

(76) Inventor: David John Maudsley, 18 Common Lane, Kenilworth, Warwickshire CV8 2ER (GB)

(*) Notice: Subject to any disclaimer, the term of this patent is extended or adjusted under 35 U.S.C. 154(b) by 0 days.

(21) Appl. No.: 09/269,686

(22) PCT Filed: Sep. 30, 1997

(86) PCT No.: PCT/GB97/02691

§ 371 Date: Mar. 30, 1999

§ 102(e) Date: Mar. 30, 1999

(87) PCT Pub. No.: WO98/14205

PCT Pub. Date: Apr. 9, 1998

(30) Foreign Application Priority Data

Sep. 30, 1996 (GB) .................................................. 9620350

(51) Int. Cl.[7] ............................ C12N 15/85; C12N 15/80
(52) U.S. Cl. .................... 424/93.2; 424/93.1; 424/93.21; 424/325
(58) Field of Search .................................. 424/93.1, 325, 424/93.2, 93.21

(56) References Cited

FOREIGN PATENT DOCUMENTS 942187    9/1994  (WO).
9531107   11/1995 (WO).

OTHER PUBLICATIONS

Liou et al. Science Mar. 30, 1990 vol. 247, No. 4950; 1581–1584.*
Kieran et al. Cell Sep. 7, 1990 vol. 62, No. 5: 1007–1018.*
Melief et al. Cancer Cells, Apr. 1990 vol. 2, No. 4: 116–120.*

* cited by examiner

*Primary Examiner*—Geetha P. Bansal
(74) *Attorney, Agent, or Firm*—Saliwanchik, Lloyd & Saliwanchik

(57) ABSTRACT

A cancer immunogen comprises foreign MHC molecules and additionally one or more oncognes (or constructs that will produce an antigenic region thereof) which can be used to immunize against tumors containing the same or similar oncogenes. Where pathogen-free allogeneic cells are used, it may not be necessary to kill the vaccine before it is administered. The efficacy of the vaccine may be enhanced if the cells also contain immunoenhancing molecules, tumor antigens, or third-party antigens. Cell vaccines containing oncongens can be standardized and used to treat (risk of) specific cancers where there are analogous oncongenes in the tumor or pre-cancerous cells. A panel of such cells covering different oncogenes may be used. The vaccines can be used to immunize prophylactically, in conduction with other therapy, post-surgery or on their own.

8 Claims, No Drawings

CANCER THERAPY USING AN ONCOGENE PRODUCT AND A FOREIGN MHC MOLECULE

FIELD OF THE INVENTION

This invention relates to the treatment of cancer and in particular to the production and use of a vaccine against tumour cells.

BACKGROUND OF THE INVENTION

Generally, a tumour is a swelling caused when a cell escapes the controls that regulate growth and division, allowing the production of excess cells. For a cell to become tumorigenic, evidence suggests that it must undergo (a number of) mutations to its genes. Genes that contribute in some way to the tumorigenic transformation of cells are called oncogenes, for example ras, p53 or HER2/neu. Approximately 20% of all human tumours have a point mutation in one of the ras genes (Barbacid (1987) *Annual Review of Biochemistry*, 56, 779–827) and about 50% have a point or structural mutation to p53 (Harris (1991) *Nature* 350,377–378). Such gene mutations are reflected in the production of abnormal proteins. It is generally recognized that an immune response might be generated to attach the tumour cell(s), if these abnormal gene products could be identified as such by the immune system.

The immune system has various weapons in its armoury; amongst these are the T cells. T cells recognise complexes of Major Histocompatibility Complex MHC) molecules and processed peptide fragments from internal proteins after these peptides have been carried to the cell surface by the MHC molecules. This enables the T cells to recognise and eliminate cells containing (intracellular) pathogens or other "foreign" antigens. MHC molecules include MHC genes, mRNA, peptides and proteins; however, it is the MHC proteins that present antigen.

In man, MHC genes and products are called HLA genes and products.

In the case of tumour cells, the "foreign" material or antigen can come in a variety of different forms, including the following:

(1) Antigen from a virus causing the tumour (at least in part);

(2) Embryological or developmental antigens expressed by the tumour;

(3) Differentiation molecules or antigens which may be expressed by that particular type of tumour (e.g. melanomas);

(4) Products of oncogenes and/or higher levels of oncogene products in transformed tumour cells.

Theoretically, it should be possible to immunize a patient against any of these four groups of antigens generating a corresponding T cell immune response. Groups 1–3 encompass essentially all of what has previously been covered by the term "tumour antigen" (*see Boon et al* (1995) *Immunology Today*, 16,334–336).

If an effective immune response is to be generated, it must avoid simply selecting for tumour cells that no longer express the particular antigen-antigen loss variants of the tumour. This would allow the cancer to return. However, a more effective response may be obtained for the oncogene products (category 4), because the oncogene products are required for the tumorigenic transformation of cells, which means that antigen loss variants either will not occur, or will not be tumorigenic.

Various strategies have been tried to produce an immune response to the products of oncogenes. A (T cell) immune response will have to be specific to the antigen, and so it will be necessary to identify the actual antigen present in the tumour cells. Specific mutations in the oncogenes can be screened for in a variety of ways, for example using mutation-specific monoclonal antibodies, probing with oligonucleotides or utilizing the polymerase chain reaction (PCR), to reveal information about (potential) tumour antigens for each specific patient.

Since most oncoproteins (the products of oncogenes such as ras) are intracellular proteins, the appropriate immune response is a T cell response requiring MHC molecules of the tumour cell to present antigen. Three problems arise in tumour cells:

(a) tumours are often immunosuppressive;

(b) tumour cells often have lost (or at least have reduced levels of MHC molecules; and (c) levels of antigen may be low.

Immunization must therefore overcome the immunosuppression of the tumour cells, provide suitable MHC antigens, and supply adequate quantities of antigen, in order to produce an effective immune response. Immunological theory is generally that the antigen must be presented to the T cells by "self" MHC molecules, i.e. MHC molecules which are encoded for and produced by the individual itself. Current approaches centre on either immunising with synthetic peptides of the oncogenes or generating HLA-matched peptide specific cytotoxic T lymphocytes (CTL) (Boon et al (1994) *Ann Rev Immunol* 12, 337–365; Finn (1993) *Current Opinion in Immunology* 5, 701–704).

Immunization with peptide (WO 92/14756) alone or in adjuvant has been found to provide only limited protection against tumours.

In order to improve immunization, peptides can be pulsed onto autologous antigen presenting cells (APC) and used as a vaccine (WO 94/21287; Crabbe et al (1995) *Immunology Today* 16, 117–121), but, due to HLA variation, it is difficult to standardise (i.e. to produce a vaccine which will be HLA compatible for random individuals). Further, obtaining fresh APC for each patient is somewhat cumbersome and time-consuming (Yanuck et al (1993) *Cancer Res.,* 53, 3257–3261). Moreover, it is generally believed that APCs cannot be taken from other people, or at least not without rigorous MHC matching, as there is so much variation in MHC genes that every individual has, for practical purposes, a unique combination of HLA alleles.

Alternatively, if T cells can be generated to the products of the oncogenes, they might be used to treat the cancer. Again, it is generally understood that the cells would have to be the patient's own cells, or clearly MHC-matched, and hence this method would be difficult to standardize.

A completely different approach would be to somehow take the patient's own tumour cells and try to use them to immunise against the residual tumour cells. Experimentally, such cells could be made more efficient at presenting the antigen and stimulating an immune response by treating them in various ways, for example transfecting them with various genes (e.g. B7), or immunising together with adjuvants, cytokines or additional strong antigens. The cells would have to be killed first to eliminate the risk of simply injecting tumour cells, thereby causing more tumours.

Since according to immunological theory, an antigen must be presented to the T cells by "self" MHC molecules, there is a strict requirement for self MHC molecules, and tumour cells from other individuals could not be used, or at least not without rigorous MHC matching.

In studies into the treatment of melanoma, melanoma cells from unrelated individuals have been used as a source of melanoma-specific antigen (Morton et al (1996), Tumour Immunology, Ed. Daigleish and Browning, CUP, Cambridge 241–268). Surprisingly, this has had some clinical success, but not without concerns from immunologists and attempts to at least partially match MHC antigens.

In addition, only a very limited array of melanoma-associated antigens (i.e. group 3 above) was chosen, and it is possible that the immune system will not recognise tumour cells that have lost these or are expressing different antigens. This will result in recurring tumours (Kim et al (1992) Int. J. Cancer 51, 283–289). This problem was recognised in WO 95/31107 which discloses a tumour vaccine comprising allogeneic cells expressing cytokines and an array of tumour-associated antigens encoded by a patient's own genomic DNA. The usefulness of this method is limited as many tumour-associated antigens are required and the antigens must be derived from the patient's own tumour cells.

There remains, therefore, a need for a simple vaccine which can elicit a strong immune response for the treatment of tumours.

SUMMARY OF THE INVENTION

The present invention is based, at least in part, on the realisation that tumors expressing an oncogene may be prevented or treated by administering to a mammal an immunogen comprising MHC molecules foreign with respect to the mammal and an expression product of at least an immunogenic region of the oncogene. It will be understood that the immunogenic components may be administered as such or in a form that provides them in vivo, e.g. by expression or induction.

Preferably the immunogen is a cell that presents, or is capable of expressing, the immunogen components. The cells used in the invention may be allogeneic, i.e. of the same species, or xenogeneic, i.e. of a different species.

When administered, the immunogen can elicit a vigorous T-cell response, which in turn contributes to the elimination of the tumour cells of the mammal.

If cells are used as the immunogen, they may be administered live, without the risk of producing further tumours. In addition, MHC matching with the mammal is not necessary.

The oncogenes expressed in the cells may be either cellular oncogenes or viral oncogenes. Preferably, the oncogenes are derived from the ras family of oncogenes.

DETAILED DESCRIPTION OF THE INVENTION

The invention will be described by way of example only with reference to cellular immunogens, as the preferred embodiment of the invention. If the essential components of the immunogen are used in a cell-free form, they may be obtained by techniques known to these of ordinary skill in the art.

The cells used in the present invention may be described as cellular immunogens. They can be made by taking a suitable cell line (eg. MRC-5, HeLa cells, VERO cells, etc.) or fresh human cells (eg. umbilical cord cells), and transforming them (for example by using a retrovirus vector, calcium phosphate precipitation or electroporation) with a suitable oncogene, preferably with a strong promoter for the gene (see Barbacid (1987) and below).

Selection of the resulting transfected cells may be by cell transformation (for example ras-transformed cells have a transformed phenotype and usually outgrow untransformed cells, at least in the mouse) or co-selection of a selectable marker (eg. neo) probably followed by cloning and screening. Alternatively, if available, cells already containing a suitable oncogene may be used. The cells may also bve transformed with additional mutated antigen(s), or tumour-specific transplantation antigen (a developmental or differentiation antigen).

The cells that may be used in the invention comprise those that contain genes for MHC molecules that are foreign with respect to the MHC molecules of the mammal. They include primary cells, primary cell lines, cell lines kept under pathogen-free conditions, such as cell lines derived for the purpose of growing viruses for vaccine purposes (e.g. MRC-5 or a more ethical equivalent or replacement), established cell lines kept under pathogen-free conditions (again, for example, cell lines derived for the purpose of growing viruses for vaccine purposes) and tumour cells. Another example is a cell that is manufactured to express a foreign MHC antigen molecule. The cells may be allogeneic or xenogeneic. In certain cases, it may be preferred that the cells are human cells. Certain established cell lines would not be suitable as live vaccines, unless they were 'cleaned up' and certified safe for vaccine purposes first (e.g. HeLa cells, HL 60 cells) (see WHO Technical Report Series (1987) volume 747, 93–107 and 1994, volume 840,100–201, WHO, Geneva).

The genetic information added to the cells may be for a viral oncogene or a cellular oncogene. Tumour suppressor genes may also be used.

The oncogenes that can be used include K-ras, H-ras and N-ras, with point mutations in codon 12 or 13. For example, amino acid 12 may be changed from Gly to Val, Ser, Arg, Cys, Asp, Ala or any other amino acid, or amino acid 13Gly to Asp. Mutations at position 61 can also be used.

Alternative constructs that include the region encoding the mutated amino acid, with or without additional amino acid sequences, may be used. For example, a gene encoding the first 20 amino acids of a mutated K-ras, followed by the amino acids of IL 2, IL 12 or IFN gamma may be used.

The genes are not restricted to those having the naturally-occurring codons for these amino acids or peptides.

Other oncogenes include p53, where mutations often involve deletions. Here the gene used to produce an effective vaccine is expected to require the region encompassing the mutation. The same applies for fusion genes, e.g. $p210^{BCR\text{-}ABL}$. Non-mutated but still antigenic regions of some oncogenes may also be used.

To elicit the correct immune response, the oncogenes in the cells must be from the same class as the tumour-associated oncogene in the mammal, i.e. if the tumour contains a K-ras oncogene, then the cells administered to the patient should also contain a gene or peptide corresponding to an immunogenic region of a K-ras oncogene. More accurately, it is the expression product of the oncogene that will be immunogenic; however, it is preferred that the cells comprise the oncogene, enabling expression of the product in vitro or in vivo. It is not necessary for the oncogene in the cells to be derived directly from the tumour in the mammal. Additional oncogenes from the same or a different class may also be present in the cells.

Other genes that might be present in the cells include genes that are helpful in generating the cell line (e.g. selection markers), suicide genes (e.g. HSVtk for use with Gangciclovir which may be valuable for providing even more safety when immunising with live cells) and genes for immune molecules (e.g. strong antigens such as HB core antigen; antigen-presenting molecules such as B7; or lymphokines such as IL 12, gamma interferon).

The cells may be killed prior to administration, e.g. by irradiation or mitomycin C treatment. However, since the cells used in this invention are, as far as is practicable and necessary for vaccine purposes, pathogen-free and also express foreign MHC molecules, they can be administered as live (i.e. replication-competent) cells.

The cellular immunogen may be used prophylactically, post-surgery to prevent relapse, in conjunction with another treatment, or on its own to provide effective treatment of tumours. The amount of immunogen that is required for effective treatment can readily be determined by one of ordinary skill in the art, as may types of formulation for administration, by vaccination.

The invention is now further illustrated by the following Example.

C3H 10T½ (Reznikoff et al (1973)*Cancer Res.* 33, 3231; H-$2^k$ haplotype) and BALB/c3T3 (Aaronson and Todaro (1968) *J. Cell Physiol.* 72, 141; H-$2^d$ haplotype) fibroblasts were obtained from the American Type Culture Collection (ATCC, Rockville, Md.). Cells were transfected with Ψ2 packaged v-Ki-ras-containing Ki-MuSV as described previously (Maudsley and Morris, 1998, *J. Exp. Med.* 167, 706–711) producing C3H 201 and Ki-BALB/c respectively.

An EJ-Ha-ras-transformed derivative of C3H 10T½ (EJ-10T½) was produced by co-transfecting 5×$10^5$ cells with 30 μg pEJ6.6 (1982, *Cell*, 29, 161) and 10 μg pSV2neo (1982, *J. Mol. Appl. Genet.*, 1, 327) by calcium phosphate precipitation followed by selection in geneticin.

C3H 10T½ cells transformed with v-Ha-ras (v-Ha-10T½) were derived by infecting C3H 10T½ cells with Ψ2- packaged (i.e. helper virus-free) retroviral vector containing the oncogene co-linear with the selection marker neo, followed by selection in geneticin.

C3H 201 and EJ-10T½ are both highly tumorigenic in C3H/He mice with similar tumorigenicity: typically $10^6$ cells give tumours in 100% of mice and $10^5$ cells in approximately 90% of mice. Ha-10T½ cells were less tumorigenic.

Male, 6–8 week old C3H/He mice were either injected with $10^6$ live Ki-BALB/c cells subcutaneously (s.c.), left unimmunised or immunised with Ha-10T½ cells. After 2 weeks mice were challenged with $10^6$ C3H 201 cells subcutaneously or $10^6$ EJ-10T½ cells injected s.c. in the flank. The mice were monitored regularly for tumour growth and were humanely killed before there was any risk of their suffering and not later than when the tumour reached 25 mm in diameter. The results of the experiments are shown in Table 1.

TABLE 1

| | challenged cells | | | |
|---|---|---|---|---|
| | C3H 201 | | EJ-10T½ | |
| Immunisation | 14 days (2 wks) | tumour progression | 14 days | tumour progression |
| none | 10/10 | 10/10 | 10/10 | 10/10 |
| Ki-BALB/c | 2/10* | 0/10 | 9/9 | 9/9 |
| Ha-10T½ | 8/9 | 9/9 | 9/9 | 9/9 |

$10^6$ C3H 201 and EJ-10T½ cells injected s.c. produced tumours in all unimmunised and Ha-10T½ cell immunised mice as expected. These tumours grew progressively. EJ-10T½ cells produced tumours also in nice immunised with Ki-BALB/c. Surprisingly, only 2 out of 10 C3H/He mice immunised with Ki-BALB/c cells and challenged with C3H 201 grew tumours at any time, and these were small and regressed. These tumours disappeared within 4 weeks.

These results are surprising, since it was assumed that the oncoprotein must be presented to the mouse's immune system by self MHC antigens (H-$2^k$) and the Ki-BALB/c cells are of the H-$2^d$ haplotype. This approach appears to be effective in preventing the growth of highly tumorigenic cells in laboratory mice.

What is claimed is:

1. A method for the prevention or treatment of an oncogene-associated tumor in a mammal, wherein said method comprises the administration of an effective amount of an immunogen to said mammal, wherein said immunogen comprises MHC molecules foreign with respect to said mammal and an expression product of an immunogenic region of an oncogene of the same class as the oncogene associated with the tumor in said mammal, but which is not derived from the tumor in said mammal.

2. The method according to claim 1, wherein said immunogen is a cell.

3. The method according to claim 2, wherein said immunogen is an allogeneic cell.

4. The method according to claim 2, wherein said immunogen is a xenogeneic cell.

5. The method according to claim 1, wherein said oncogene is a cellular oncogene.

6. The method according to claim 1, wherein said oncogene is a viral oncogene.

7. The method according to claim 1, wherein said oncogene is ras, p53, or HER2/neu.

8. The method according to claim 1, wherein said mammal is a human.

* * * * *